(12) United States Patent
Bentley et al.

(10) Patent No.: US 7,994,311 B2
(45) Date of Patent: Aug. 9, 2011

(54) FLUORESCENT CHEMOSENSORS FOR METALS BASED ON DIPYRRINS

(75) Inventors: Paul A. Bentley, Albuquerque, NM (US); Yujiang Mei, Albuquerque, NM (US)

(73) Assignee: STC. UNM, Albuquerque, NM (US)

( * ) Notice: Subject to any disclaimer, the term of this patent is extended or adjusted under 35 U.S.C. 154(b) by 952 days.

(21) Appl. No.: 11/879,566

(22) Filed: Jul. 17, 2007

(65) Prior Publication Data
US 2008/0182333 A1    Jul. 31, 2008

Related U.S. Application Data

(60) Provisional application No. 60/831,391, filed on Jul. 17, 2006.

(51) Int. Cl.
C07B 47/00 (2006.01)
G01N 33/20 (2006.01)
C07D 207/18 (2006.01)
C07D 207/232 (2006.01)

(52) U.S. Cl. ............. 540/145; 436/80; 436/81; 436/83; 436/84; 548/564; 548/565

(58) Field of Classification Search ............. 436/80, 436/81, 83, 84; 548/402, 564, 565; 540/145; 438/962
See application file for complete search history.

(56) References Cited

U.S. PATENT DOCUMENTS
2004/0254383 A1 * 12/2004 Yu et al. ............. 548/402
* cited by examiner Primary Examiner — Ling-Siu Choi
Assistant Examiner — Monique Peets
(74) Attorney, Agent, or Firm — Bauman, Dow & León, P.C.; Alberto A. León (57) ABSTRACT

The present invention is a new class of fluorescent sensor with unprecedented sensitivity, selectivity and synthetic efficiency for the identification and qualitative and quantitative detection of transition metal ions. The chemosensing properties are based on an internal charge transfer mechanism or photoinduced electron transfer and are effective in vitro. The chemosensor comprises one or more electron donating dipyrrin functionalities linked to an electron withdrawing functionality. The chemosensor forms a stable transition metal complex through internal charge transfer between the electron donating functionality and the target transition metal, which results in measurable fluorescence. Specific examples for sensing zinc and copper ions are described.

13 Claims, 10 Drawing Sheets

Fig. 1

| entry | metal cation | ligand | $\Phi_{complex} \times 10^{-4}$ | $\Phi_{complex}/\Phi_{ligand}$ [a] |
|---|---|---|---|---|
| 1 | 5 equiv. $Zn^{2+}$ | 2 | 66.4 | 14.1 |
| 2 | 50 equiv. $Zn^{2+}$ | 2 | 95.1 | 20.1 |
| 3 | None | 2 | 4.7 | 1.0 |
| 4 | 5 equiv. $Na^+$ | 2 | 4.8 | 1.0 |
| 5 | 5 equiv. $K^+$ | 2 | 4.7 | 1.0 |
| 6 | 5 equiv. $Mg^{2+}$ | 2 | 5.9 | 1.2 |
| 7 | 5 equiv. $Ca^{2+}$ | 2 | 4.4 | 1.0 |
| 8 | 5 equiv. $Fe^{3+}$ | 2 | 7.4 | 1.6 |
| 9 | 5 equiv. $Co^{2+}$ | 2 | 5.3 | 1.1 |
| 10 | 5 equiv. $Ni^{2+}$ | 2 | 5.3 | 1.1 |
| 11 | 5 equiv. $Cu^{2+}$ | 2 | 10.7 | 2.3 |
| 12 | 5 equiv. $Cd^{2+}$ | 2 | 7.3 | 1.5 |
| 13 | 50 equiv. $Zn^{2+}$ | 3 | 265.7 | 7.6 |
| 14 | None | 3 | 34.9 | 1.0 |
| 15 | 50 equiv. $Zn^{2+}$ | 4 | 2120.2 | 68.2 |
| 16 | None | 4 | 31.1 | 1.0 |

# FLUORESCENT CHEMOSENSORS FOR METALS BASED ON DIPYRRINS

CROSS-REFERENCE TO RELATED APPLICATION

I hereby claim the benefit under Title 35, United States Code Section 119(e) of any United States Provisional Application(s) listed below:
Application No. 60/831,391
Filing Date: Jul. 17, 2006

BACKGROUND OF THE INVENTION

1. Technical Field of the Invention

This invention generally relates to sensors, more specifically to chemical sensors, still more specifically to chemical sensors for metals, and further more specifically to fluorescent chemical sensors for metals based on dipyrrins.

2. Description of the Background Art

Zinc and copper ions both play important roles in biological systems. However, they are also chemical pollutants of the environment. Accordingly, detection of trace amounts of zinc and copper ions is of great importance in environmental and biological analyses. Biosensors play an increasingly important role in understanding biological processes and in determining the physiological state of cells and tissues.

Zinc

Biosensors are essential for the analysis of free $Zn^{2+}$ because that metal is unresponsive to spectroscopic interrogation. The zinc ion is the second most abundant heavy metal ion and well known to play an important role in cellular events including structural co-factors, regulator of enzymes, DNA binding, catalytic centers and neuronal signal transmission. Zinc is also a well-known metal pollutant of the environment. Too much zinc may reduce the soil microbial activity causing phytotoxic effects[3] and it is a common contaminant in agricultural and food wastes. Therefore, the ability to detect and quantify trace amounts of $Zn^{2+}$ in biological systems as well as in the environment is of great analytical importance.

One way that trace amounts of $Zn^{2+}$ can be detected and quantified is using chemical sensors. Chemical sensors or chemosensors present distinct advantages over other methods of detection. For example, chemosensors can be designed to selectively detect and quantify trace amounts of metals, such as $Zn^{2+}$. Chemical sensors use the well known principle of receptor/substrate affinity. The chemosensor is a receptor, which can recognize, detect and measure a target metal by virtue of the chemosensor's selective affinity to the particular metal.

During the past decade, a great deal of effort has been directed toward the development of selective ligands for $Zn^{2+}$, such as quinoline based ligands, bis(2-pyridylmethyl) amine, acyclic and cyclic polyamines, and others. Looking for the new selective and simple ligands for $Zn^{2+}$ is still a design and synthetic challenge. The goal is to design a chemosensor molecule or family of molecules which can selectively detect and measure $Zn^{2+}$ over other metal cations which exhibit high interference from $Zn^{2+}$.

The prior art discloses several chemosensors for zinc and copper ions. Since Fischer found that dipyrrins can form stable complexes with divalent metal ions in 1924, various complexes of dipyrrins with metals have been prepared.

The internal charge transfer (ICT) mechanism has been successfully utilized in connection with chemosensors. The ratiometric technique has seen a widespread use in biological, polymetric, and sensory materials chemistry. The significant advantages of this technique include reduced artifacts, increased precision and dynamic range with a built-in correction for environmental effects. Consequently, the development of ratiometric $Zn^+$ chemosensors has emerged as an important area in molecular design and synthesis.

A milestone in the development of chemosensors for $Zn^{2+}$ was 6-methoxy-8-p-toluenesulfonamidoquinoline (TQS), which was first applied to detect $Zn^{2+}$ in 1987. However, the usefulness of TQS as a chemosensor was hindered by the fact that the excitation wavelength of TQS and its derivatives was not in an optimal UV range. Long-wavelength absorption and emission may be more useful for significantly reducing background absorption, fluorescence and light scattering.

Copper

Like Zinc, Copper has been shown to be a metal of biochemical significance e.g. copper-zinc superoxide dismutase's role in the enzymatic defense against oxygen toxicity. Furthermore, and also like Zinc, copper has been identified as a significant enviromental pollutant. Logically, then, the ability to detect and measure trace amounts of $Cu^{2+}$ has obvious implication in environmental and biological analysis.

The 8-hydroxyquinoline (8-HQ) moiety has been one of the most useful ionophores, used in a variety of investigations involving metal ion recognition. In recent years, many chemosensors based on 8-HQ have been developed for $Zn^{2+}$, $Cd^{2+}$, $Pb^{2+}$, $Hg^{2+}$. However, use of 8-HQ derivatized chemosensors for the detection of $Cu^{2+}$ has not been exploited. Chemosensors that have displayed selectivity for $Hg^{2+}$ have also shown a much more limited fluorescent change in the presence of $Cu^{2+}$. $Hg^{2+}$ has a larger atomic radius than $Cu^{2+}$, thus by increasing the steric hindrance around the binding site (8-HQ), a significant enhancement in the selectivity for $Cu^{2+}$ compared to $Hg^{2+}$ is achievable.

Dipyrromethenboron difluoride (difuoroboradiaza-s-indacene, BODIPY) has been widely used as fluorescent dyes. They have relatively high fluorescence quantum yields, good photo-stabilities and absorption coefficients. Long-wavelength absorption and emission have been shown to significantly reduce background absorption, background fluorescence, and light scattering. Maximal fluorescence emission was tunable to longer wavelength by extending the conjugation and rigidification of the BODIPY core.

SUMMARY OF THE INVENTION

The invention disclosed and claimed in the present application comprises a new class of sensor for the identification and qualitative and quantitative detection of transition metal ions of unprecedented sensitivity, selectivity and synthetic efficiency, which is effective in vitro. One chemosensing property of some of the chemical compounds disclosed and claimed in this application is based on an internal charge transfer mechanism. Upon addition of the metal to the chemosensor compounds, a shifted fluorescent emission can be observed by optical responses and is attributed to the capture of the metal ion by a dipyrrin moiety leading to an altered electron-donating ability. The dipyrrin moiety disclosed and claimed herein can be symmetrical or asymmetrical.

In the early development of the class of chemosensors described and claimed in this application, applicant concentrated upon a molecule that would selectively bind $Zn^{2+}$ weakly to induce a sensitive fluorescence response over the low to mid micro-molar range with the emission spectrum observable by fluorescence microscopy. Increased steric hindrance of the sensor allows still weaker binding. Sensor cell permeability was a prerequisite, whilst the ready availability of the sensor through a direct and economical synthesis was a high priority.

Figure 1:
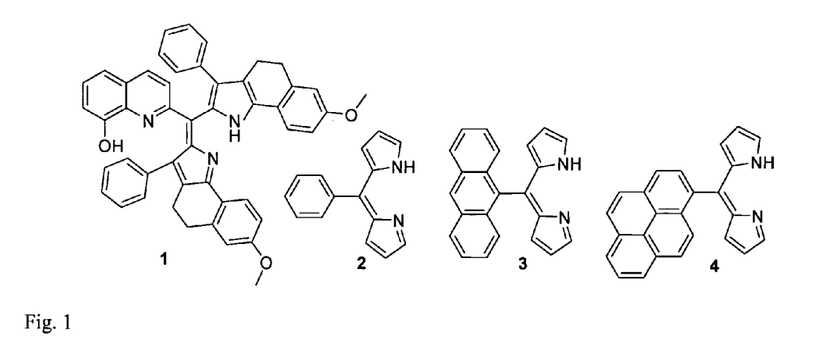

The chemosensor design focused on the dipyrrin system that was readily prepared by a simple two step protocol. Enamines conjugated with imines, such as (2), (3), and (4), are very effective at photo-induced electron transfer (PET), that minimize fluorescence quantum yield ($\Phi_F$). The binding of $Zn^{2+}$ to the dipyrrin system suppresses PET and thereby elicits fluorescence emission. Examples of dipyrrin compounds with chemosensor properties are shown in FIG. 1.

Figure 2:
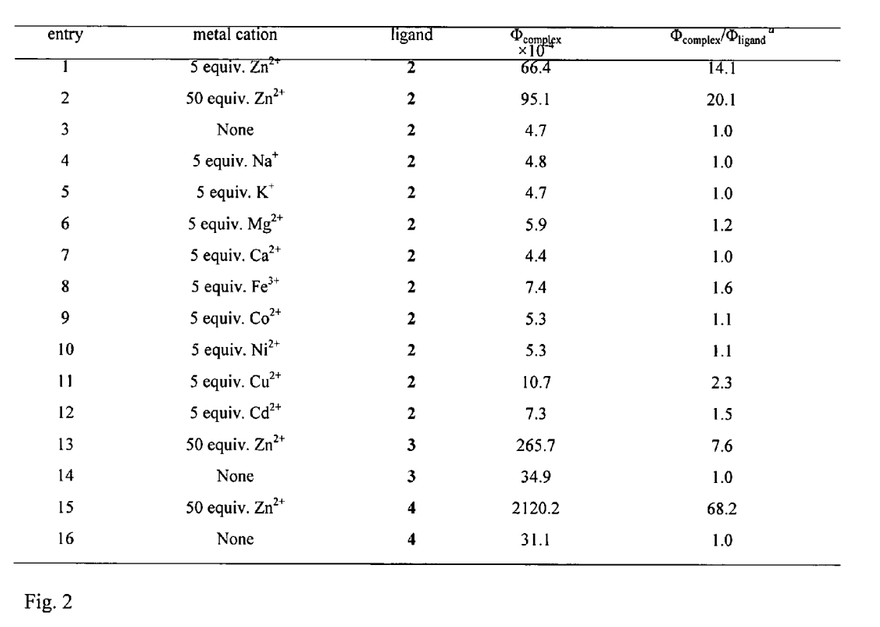
Figure 3:
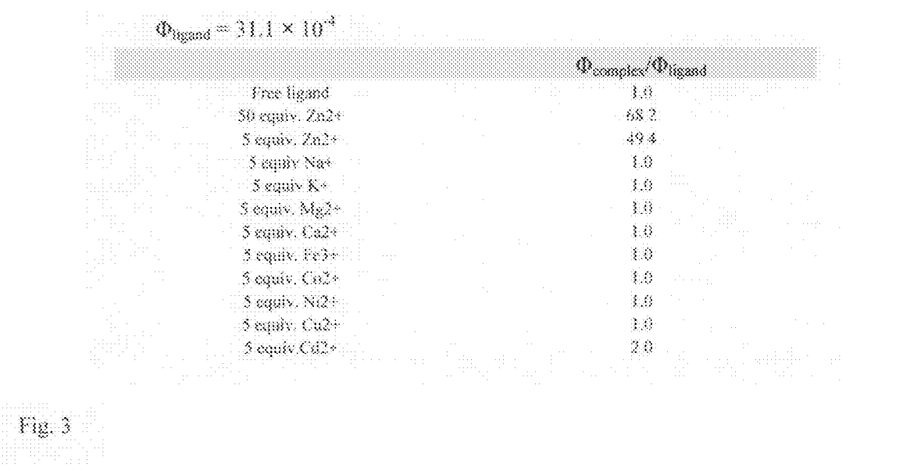
FIG. 3 (Table 2) shows ion selectivity of dipyrrin (4).

Early in the development of the family of chemosensors disclosed and claimed herein, applicant designed sensor (1) was designed to provide internal charge transfer (ICT) detection of $Zn^{2+}$. Preliminary evaluation suggested compound (1) was not optimal due to insufficient aqueous solubility. A simplified structure of 5-phenyl-4,6-dipyrrin (2) was then tested with the idea that the molecular structure of (2) would cure the solubility problems associated with (1). Compound (2) was also found to bind $Zn^{2+}$. The $Zn^{2+}$/(2) complex gave a notable quantum yield (Table 1, entry 1), that increased as the $Zn^{2+}$ concentration was elevated (Table 1, entry 2). Excellent selectivity of (2) for $Zn^{2+}$ in comparison to other common metal ions (Table 1, FIG. 2) was observed, even with $Cd^{2+}$ (Table 1, entry 11), known for a significant fluorescence emission with $Zn^{2+}$ sensors. This selectivity is surprising in light of the number of stable complexes dipyrrins have been shown to form with divalent metal ions.

The conjugated (2) comprises a fluorophore with the dipyrrin moiety behaving as an ionphore. Benzaldehyde was used to form (2) because the properties shown by this type of sensing molecule with an benzene ring are representative of the general behavior of the family of compounds. In spite of the low fluorescence quantum yields of benzene, substituting benzene ($\Phi_F$=0.05±0.02) with a more intrinsically luminescent unit can make a great improvement in $\Phi_F$. An examples of another aromatic entity used instead of benzene is anthracene ($\Phi_F$0.27±0.03). When a dipyrrin is attached to the benzene ring, the fluorescence quantum yield ($\Phi_F$) of (2) was very low and was determined to be 0.0011 due to the photo-induced electron transfer (PET), which is the intra-molecular quenching mechanism of an enamine group and an imine group in conjugate. When $Zn^{2+}$ bound with a dipyrrin moiety, PET was hindered and fluorescence emission intensity was recovered. And values of fluorescence quantum yields was determined in the reference to perylene in toluene that have a reported $\Phi_F$ of 1.32±0.02, and using the equation $\Phi_x/\Phi_s=(S_x/S_s)\times[(1-10^{-As})/(1-10^{-Ax})]$, where x and s indicate the unknown and reference solution, S is the area under the emission curve and A is the absorbance at the excitation wavelength ($\lambda_{exe}$=432 nm). After addition of 50 equiv. $Zn^{2+}$, the fluorescence quantum yield was determined to be 0.07. Fluorescence quantum yield exhibited a 65.7-fold increase.

Figure 4:
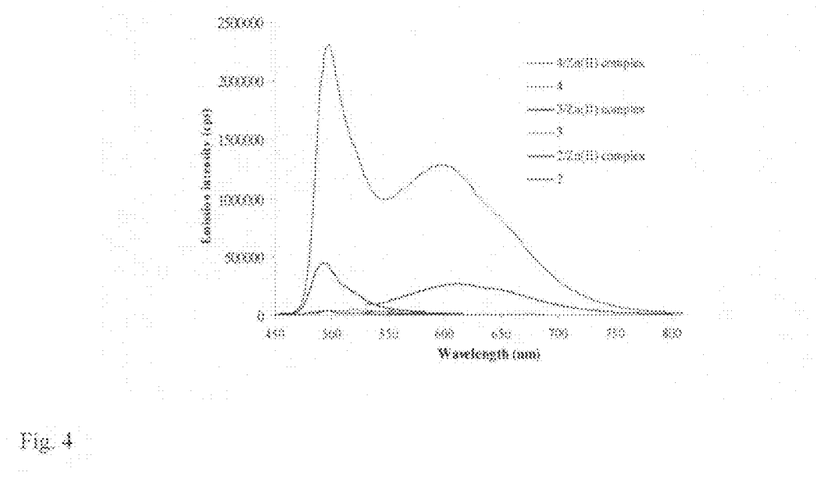
FIG. 4 is the fluorescence emission spectra for chemosensors (2), (3) and (4).
Figure 5:
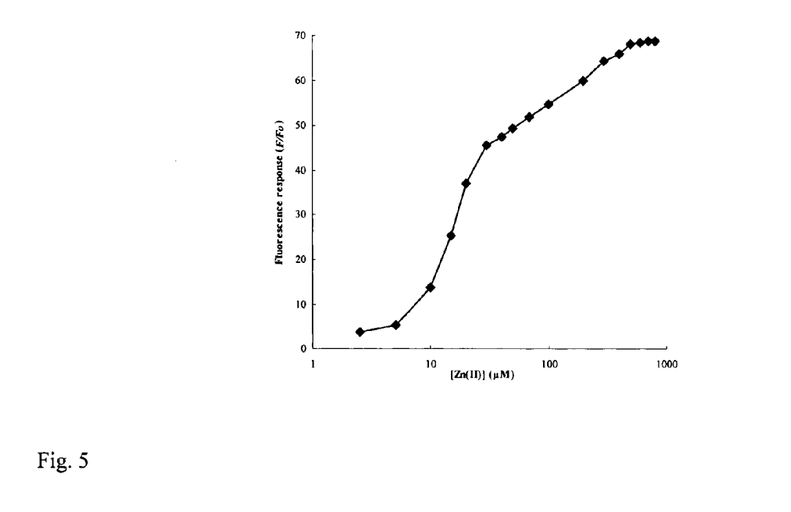
FIG. 5 is a graph of fluorescence response and $Zn^{2+}$ concentration and (4).

Although the quantum yield of the system was expected to be high, evaluation of (3) showed a surprisingly low quantum yield (Table 1, entry 13). We believe that the steric strain in conformations that would allow the orbital alignment needed for conjugation may be detrimental to high quantum yield. 1-pyrenyldipyrrin ((4), PYDPY1), is more fluorescent and sterically less demanding than (3). Upon binding $Zn^{2+}$ a remarkable 68.2 fold increase of quantum yield was observed. The fluorescence emission (FIG. 4) of (4) was found to be sensitive to $Zn^{2+}$ concentrations between 5 and 500 μM range (0.5 to 50 equivalents, FIG. 5) with a $K_d$ of 20 μM. Indeed, as a $Zn^{2+}$ sensor, (4) is unsurpassed in its effective concentration range with $Zn^{2+}$, thus providing a rarely found degree of sensitivity.

Figure 6:
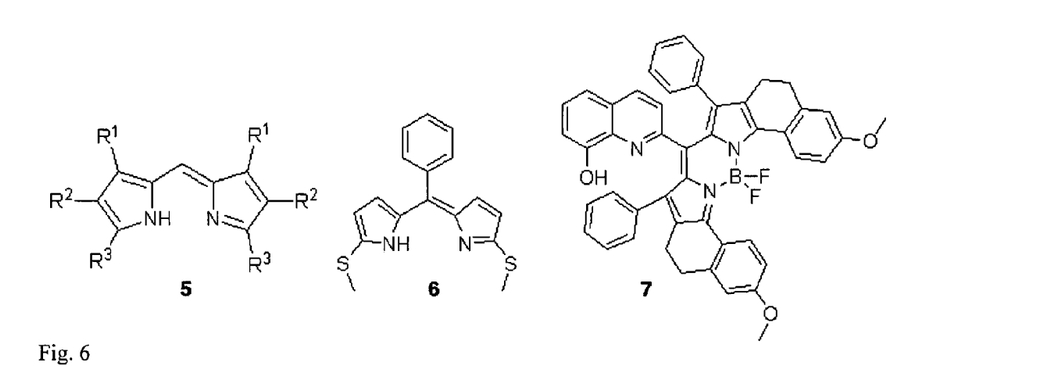
FIG. 6 depicts dipyrrin based compounds.

Dipyrrin moieties (FIG. 6) have provided the basis for boron-dipyrrin dyes, which have been widely used as fluorescent labels. Free base dipyrrins have also reacted to a wide range of metal salts to form the corresponding bis(dipyrrinato)metal(II) or tris(dipyrrinato)metal(III) complexes. Dipyrrins can form stable complexes with divalent metal ions, opening dipyrrins up to exploitation as metal chemosensors. Variation in the size of the substituents ($R^3$) at the 5,5' positions on dipyrrin (5) resulted in different configurations on formation of the metal complex, due to varying amounts of steric repulsion. Thus, the increasing size of substituents at 5,5' positions may result in a significant enhancement of selectivity for one cation. For example, (6) with 5,5' substituents as thiomethoxy groups was studied and did not afford the corresponding bis(dipyrrinato)zinc complex.

Figure 7:
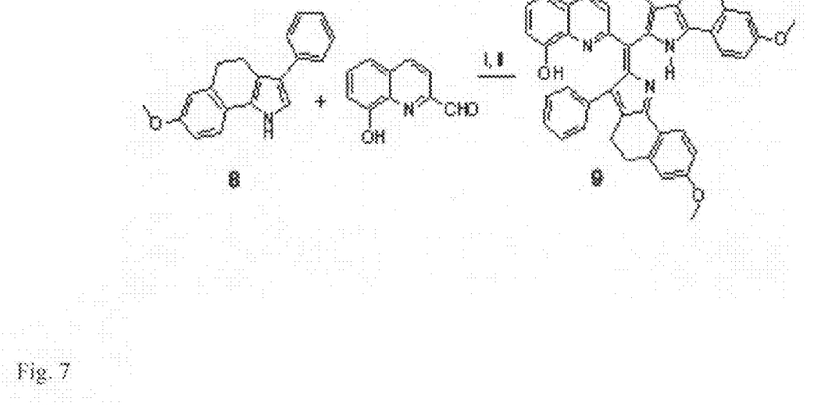
FIG. 7 is Scheme 1, the synthesis of chemosensor (9). TFA, DCM, 25° C., $N_2$ (g); ii. p-chloranil, DCM, 25° C., $N_2$ (g) overall yield 42%.

The chemosensor of the $Zn^{2+}$-sensing embodiment of the present invention comprises a molecule which incorporates dipyrrin as an electron-donating domain and the hydroxyl group of the 8-hydroxyquinoline (8-HQ) moiety as an electron-withdrawing domain. Compound (5) is easily synthesized by condensation of 8-HQ-2-carbaldehyde and compound (8) (FIG. 7, Scheme 1). Although 8-HQ has been widely used as ionophores for metal recognition, (7) does not have a high binding affinity for $Zn^{2+}$. The dipyrrin moiety of (9), on the other hand, selectively binds $Zn^{2+}$. Furthermore, capture of $Zn^{2+}$ by the dipyrrin reduces the dipyrrin electron-donating ability and measurably influences the emission properties. Chemosensor (9) has an absorption wavelength at 580 nm and an emission wavelength at 672 nm. Both absorption and emission wavelengths are in the visible region. Chemosensor (9) shows a 56 nm blue shift of fluorescence emission in the presence of $Zn^{2+}$.

Figure 8:
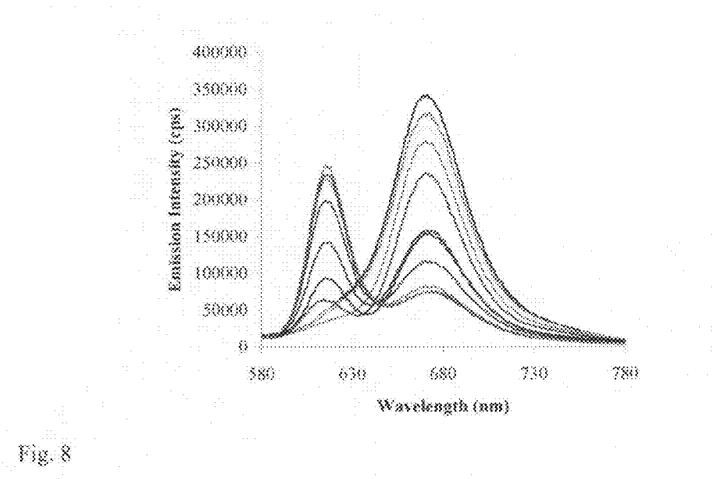
FIG. 8 is the fluorescence emission spectra of (9) in an acetonitrile solution in the presence of different concentrations of $Zn^{2+}$ (0, 2.5, 5, 10, 20, 50, 100, 200, 300, 400, 500 μM). Excitation wavelength was 550 nm. Emission wavelengths were 616 (which increased in intensity with concentration) and 672 nm (which decreased in intensity with concentration). The concentration of (9) was 5 μM.
Figure 9:
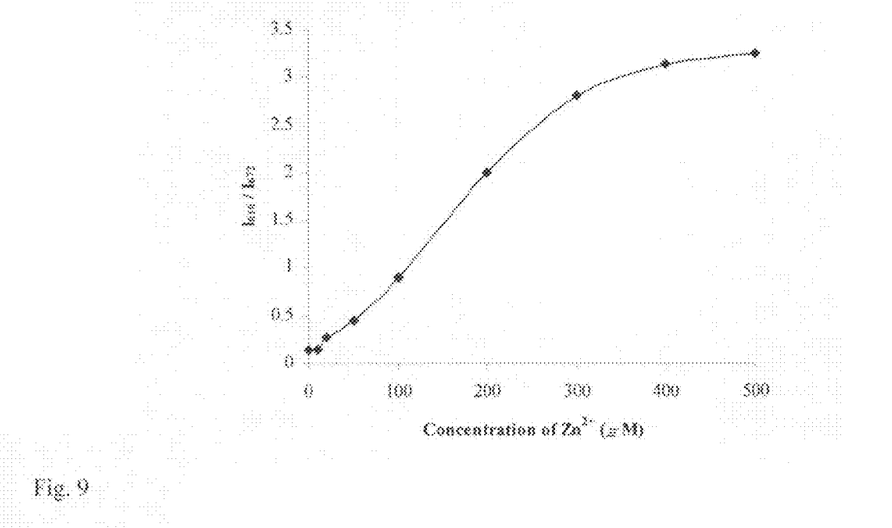
FIG. 9 is the plot of the fluorescence intensity ratio between 616 and 672 nm (I 616/I 672).

Fluorescence emission was monitored to determine the sensitivity of compound (9) towards $Zn^{2+}$ (FIG. 8). An acetonitrile solution of (9) (5 μM) was titrated with $Zn^{2+}$. Free (9) displays a band with maximum at 672 nm. With increasing concentration of $Zn^{2+}$, a decrease in fluorescence emission at 672 nm was observed whilst the emission intensity at 616 nm increased. An isoemission point was also observed at 635 nm. These data are consistent with a 1:2 $Zn^{2+}$: (9) complex. FIG. 9 shows the dependence of emission intensity ratios between 616 nm and 672 nm on the concentration of $Zn^{2+}$. Relatively low concentrations of $Zn^{2+}$(2.5, 5, 10 μM only slightly quenched the emission intensity and $I_{616}/I_{672}$ remained unchanged at 0.14. With a 20 μM concentration of $Zn^{2+}$ a clear new peak centered at 616 nm was observed and $I_{616}/I_{672}$ increased to 0.27.

Figure 10:
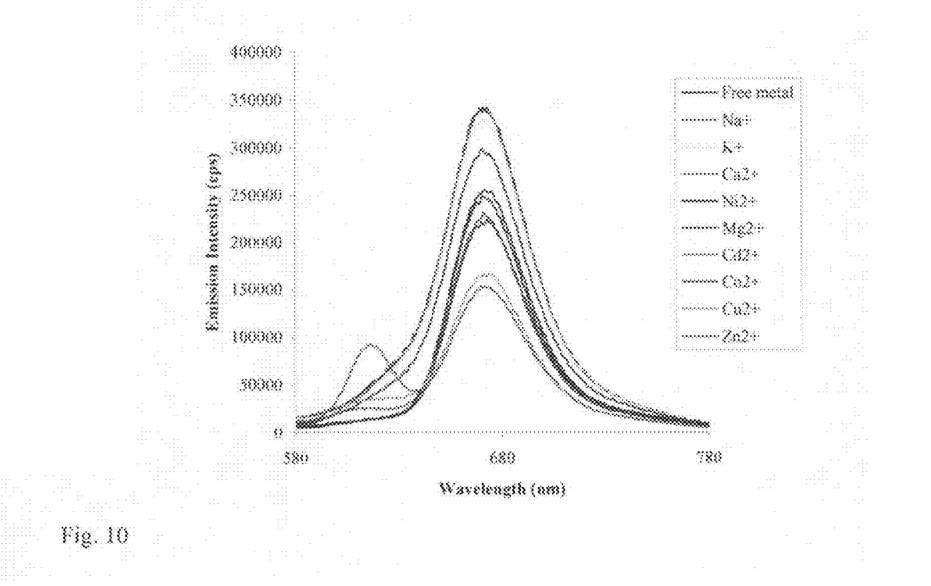
FIG. 10 is the fluorescence emission spectra of (9) (5.0 μM) in an acetonitrile solution in the presence of different metal ions (50 μM). Excitation wavelength was 550 nm. Emission wavelengths were 672 and 616 nm.
Figure 11:
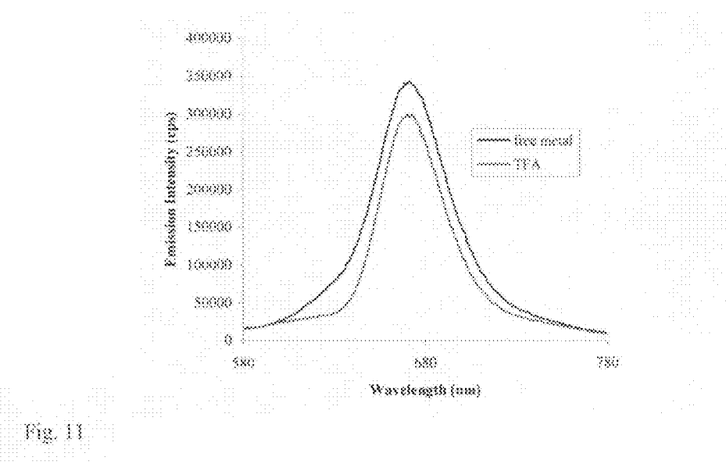
FIG. 11 is the fluorescence emission spectra of (9) (5.0 μM) in an acetonitrile solution in the presence of TFA (50 μM). Excitation wavelength was 550 nm. Emission wavelengths were 672 nm.

The selectivity of (9) was examined in an acetonitrile solution by titration of (9) with various metal ions (FIG. 10). The titration of $Na^+$, $K^+$ and $Ca^{2+}$ did not affect the emission intensity, and $Ni^{2+}$, $Mg^{2+}$, $Cd^{2+}$ and $Co^{2+}$ generated a 34%, 37%, 40%, 43% quench of emission intensity respectively. Since (7) showed no sensitivity to $Ni^{2+}$, $Mg^{2+}$, $Cd^{2+}$ and $Co^{2+}$, the emission intensities were diminished due to their low affinity with the dipyrrin moiety of (9) which has large size of substituents at the α, α positions. In contrast to other metals, $Cu^{2+}$ (50 μM) reduced emission (55%) to a similar degree as $Zn^{2+}$ at the same concentration at 672 mn. However, no blue shift was observed in the $Cu^{2+}$ binding experiment. This may be due to bind with the 8-HQ moieties and lead to an increase in the electron-withdrawing ability of the hydroxyl group (balancing the effect of dipyrrin binding).

It is known in the prior art that a proton can transfer to amino group due to the decrease of $pK_a$ values of the hydroxyl proton by chelation of metal ions. This transfer also can affect the fluorescence emission. The titration of 10 equiv. TFA only slightly diminished the fluorescence emission, and this may be due to the difficulty of proton binding with the nitrogen of imine groups in dipyrrin moiety (FIG. 10).

In summary, this application describes and claims a ratiometric fluorescent sensor for $Zn^{2+}$ based on an internal charge transfer (ICT) mechanism. The obvious blue-shift emission upon addition of $Zn^{2+}$ to (9) can be observed by optical responses, and it is attributed to the capture of $Zn^{2+}$ by a dipyrrin moiety leading to a diminished electron-donating ability.

Figure 12:
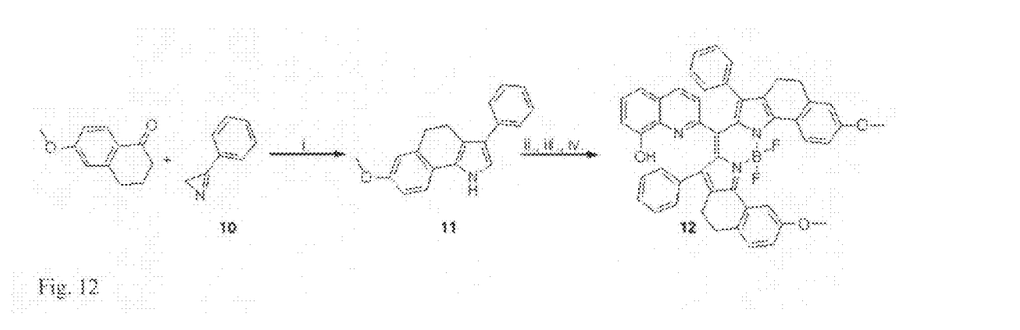
FIG. 12 shows Scheme 2, the synthesis of Chemosensor (12). (i) NaH, DMSO, 25° C., $N_2$ (g), 91%; ii. 8-hydroxyquinoline-2-carbaldehyde, TFA, DCM, 25° C., $N_2$ (g); iii. p-chloranil, DCM, 25° C., $N_2$ (g); iv. TEA, $BF_3$-$OEt_2$, 25° C., $N_2$ (g), 25% (for ii., iii., iv.).

In the copper binding embodiment of the invention, the chemosensor, (12), comprises 8-HQ moiety as a binding site and BODIPY as a reporting group. (10) was prepared from styrene by bromination, conversion to the bromoazide which was eliminated to give azidostyrene; on heating (10) was isolated. (11) was synthesized by (10)'s reaction with methoxytetralone in the presence of NaH. In a one-pot three-step conversion, 8-HQ-2-carbaldehyde was condensed with pyrrole (11) to afford the dipyromethane which was oxidized to the dipyrromethene and reaction with $BF_3$-$OEt_2$ gave chemosensor (12) (FIG. 12, Scheme 2).

The conjugated chemosensor (12) constituted a fluorophore with the 8-HQ moiety behaving as an ionphore which resulted in absorption (660 nm) and emission (680 nm) in the visible region. Chemosensor (12) had a more intense, sharper absorption band compared with a more flexible BODIPY structure. Phenyl groups were introduced to the pyrroles with the hope of creating greater steric hinderance to $Hg^{2+}$'s approach to the binding site, while $Cu^{2+}$ would bind easily with the 8-HQ moiety because of $Cu^{2+}$ relatively small atomic radius. The greater steric hinderance also helps to secure the incoming guest.

Figure 13:
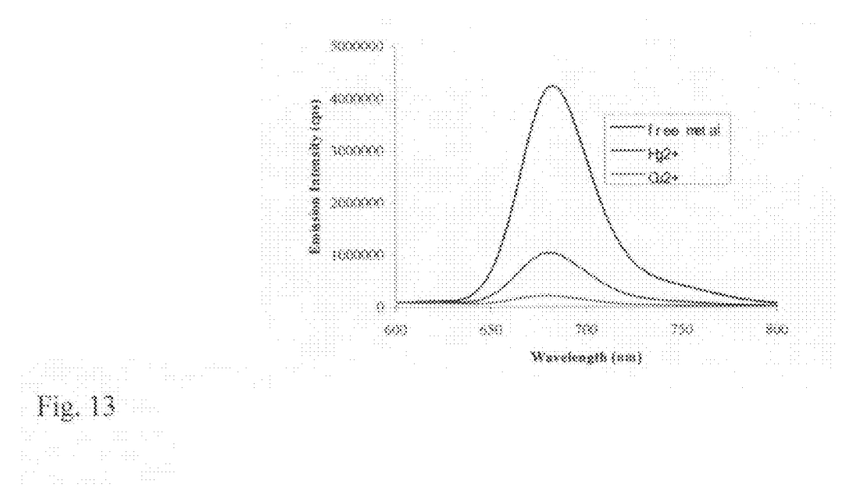
FIG. 13 shows fluorescence emission spectra of (10) (5.0× $10^{-6}$ M) in an aqueous dioxane (1:1, v/v) solution in the presence of different metal ions (5.0×$10^{-5}$ M). Excitation wavelength was 550 nm. Emission wavelength was 680 nm.

Initially, metal ion selectivity was examined in aqueous dioxane (1:1, v/v) solution. The presence of 10 equiv. of various metal ions ($K^+$, $Mg^{2+}$, $Zn^{2+}$, $Fe^{3+}$, $Ni^{2+}$, $Co^{2+}$ and $Cd^{2+}$) had a slight effect upon the (12)'s fluorescence emission spectra (less than 10%). However, $Cu^{2+}$ and $Hg^{2+}$ produced significant changes in fluorescent spectra of (12) (FIG. 13). As was expected, $Cu^{2+}$'s induced fluorescence quenching (quenched 97% by 10 equiv.) was more pronounced than $Hg^{2+}$'s (quenched 77% by 10 equiv.).

Figure 14:
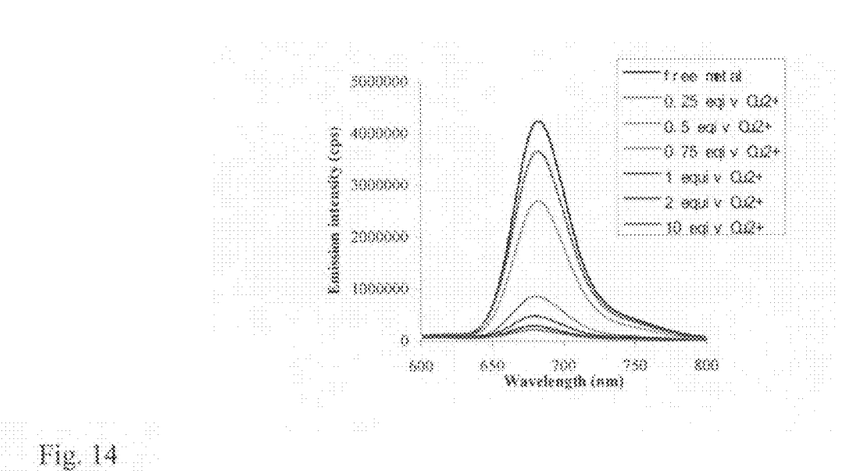
FIG. 14 shows fluorescence emission spectra (excitation at 550 nm) in an aqueous dioxane (dioxane:water=1:1, v/v) solution in the presence of different concentrations of $Cu^{2+}$.

The sensitivity of the fluorescence emission response of (12) towards $Cu^{2+}$ was subsequently examined in aqueous dioxane solution (FIG. 14). The emission intensity was quenched 95% by 2 equiv. The association constant of 12 with $Cu^{2+}$, was determined as $3.21 \times 10^5$ (assuming the formation of 1:1 complex).

In summary, (12) showed in sensitivity to numerous metal ions and displayed higher sensitivity for $Cu^{2+}$ than $Hg^{2+}$ in an aqueous dioxane solution, taking advantage of the conformationally restricted and sterically hindered BODIPY core.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

FIG. 1 depicts dipyrrin chemosensors. Compound (1) illustrates the preferred embodiment of the invention which works through an internal charge transfer mechanism. Compounds (2), (3) and (4) are alternative embodiments of the invention which work through a photo-induced electron transfer mechanism.

FIG. 2 (Table 1) shows ion selectivity and $\Phi_{complex}/\Phi_{ligand}$ of dipyrrins (2), (3) and (4). The excitation wavelengths were 432, 475, 450 nm. The emission wavelengths were 496, 612, 497 and 599 nm for (2), (3) and (4). The ratio of fluorescence quantum yield [fluorescence quantum yield of metal ion/(2), (3) or (4) complex over fluorescence quantum yield of free ligand (10 μM)] was measured in acetonitrile.

FIG. 16 displays more specific dipyrrin derivative structures for PET, as well as R4 substituents for those dipyrrin derivatives. $R^{1-7}$ may incorporate polar groups, including natural sources such as carbohydrates, amino acids, peptides or aliphatics such as ethlenehydroxy ether. The fused phenyl structure could be replaced by any of the fused Ar structures. Ar=phenyl, napthyl, anthryl, pyrenyl, pyridine, quinoline, adridine and their derivatives, as well as other aromatic strictures. Ar derivatives may include electron withdrawing groups, e.g. $N0_2$, $NR_3+$, $SO_3H$, CN, $CO_2H$, CHO, or electron donating groups, e.g. OH, OR, $NH_2$, NRH, $NR_2$, where R=carbon functionality. In the R4 substituents, any attachment of the oligoene may be H or Ar.

DETAILED DESCRIPTION OF THE PREFERRED EMBODIMENT OF THE INVENTION

The most basic embodiment of the invention is a chemosensor for metal ions that comprises a metal binding, electron donating dipyrrin functionality linked to an electron withdrawing functionality. One of the preferred embodiments is a chemosensor for $Zn^{2+}$, while alternative embodiments are chemosensors for $Cu^{2+}$ and other metal ions.

The chemosensor of this invention can be attached or absorbed onto an appropriate material, such as glass, plastic, quantum dots or polymers. Appropriate derivatization is necessary for attachment. Luminescent quantum dots have been used as alternative to organic fluorophores in bioimaging applications due to their high emission quantum yield, photostability, size dependent wavelength tunability in the visible range of the electromagnetic spectrum and narrow emission peaks, which enable simultaneous observation of multiple targets by using quantum dots of different emission wavelengths. Recently, the scope of use of luminescent quantum dots was expended through the development of quantum dot probes that are based on fluorescence resonance energy transfer (FRET) between quantum dots and organic fluorophores or gold nanocrystals immobilized on their surface. The quantum dot FRET based probes change their emission color when the organic fluorophores or gold nanocrystals are displaced from the quantum dots. The fabrication of a solid state sensor is based on the FRET interactions between quantum dots and organic fluorophores. The quantum dots and organic fluorophores are immobilized to polymer layers that are deposited on a glass surface using a layer by layer deposition (LbL) method.

Figure 15:
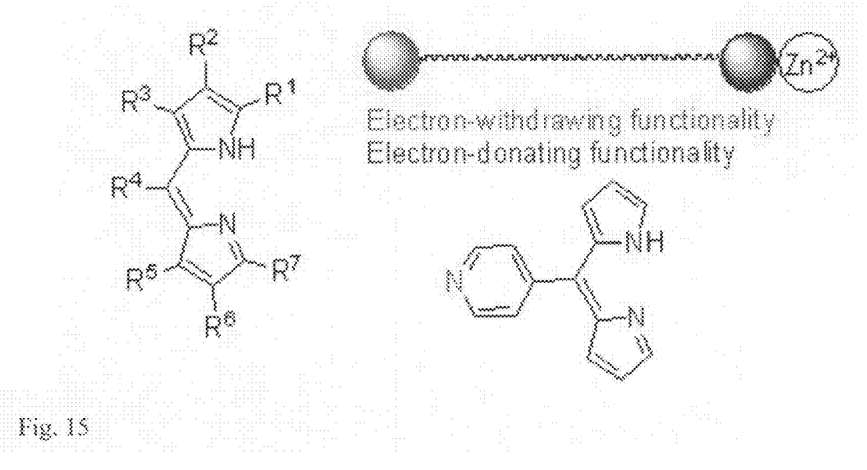
FIG. 15 depicts dipyrrin and the principle of ICT chemosensors.
Figure 16:
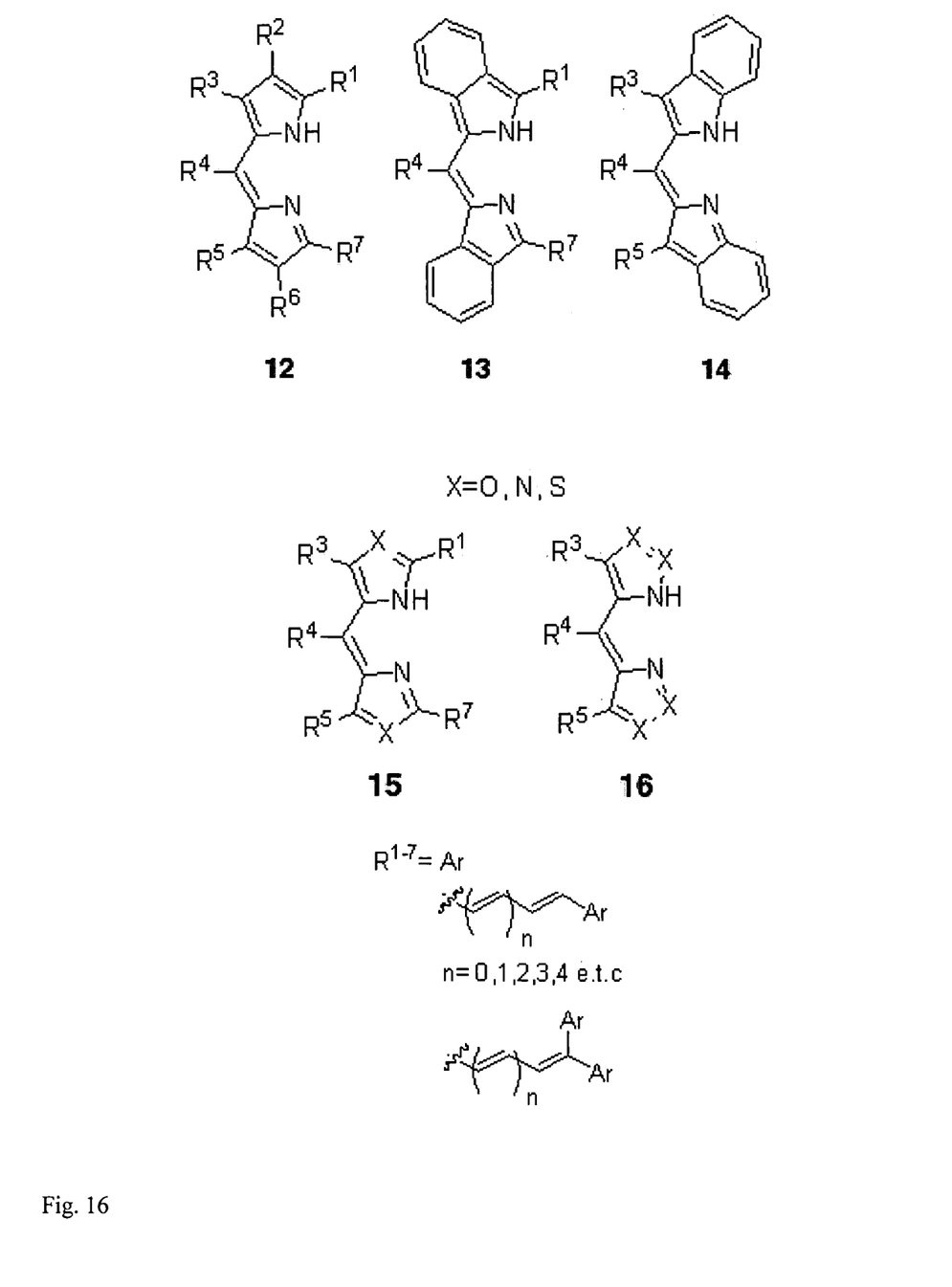
Figure 17:
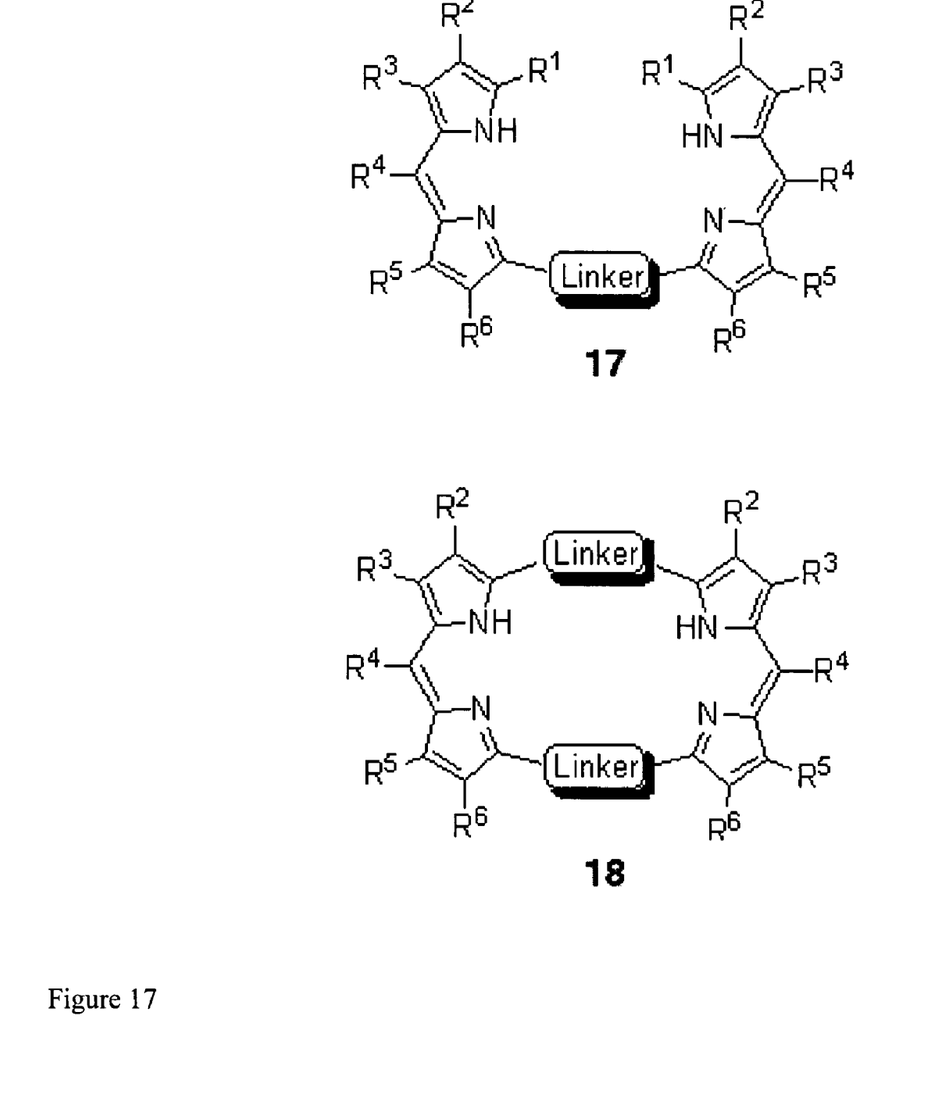
FIG. 17 depicts linked dipyrrin chemosensors. The linker may constitute aliphatic functional groups or groups for $R^{1-7}$ from FIG. 16.

In one of the preferred zinc-sensing embodiment, the dipyrrin functionality is 1-pyrenyldipyrrin (Compound 4, PYDPY1). PYDPY1 represents a new in vitro sensor structure with excellent sensitivity and unsurpassed selectivity in the low to mid micro-molar range. In alternative embodiments any dipyrrin derivative can be used in place of PYDPY1, indeed derivatives will access a wider range of concentrations that can be evaluated. Coupled with its ready availability, dipyrrin is a highly complementary tool for $Zn^{2+}$ sensing. In the alternative $Cu^{2+}$ chemosensor, the binding site is an 8-HQ moiety and BODIPY is used as the reporting site. A core concept of this patent is the use of dipyrrin (1) and its derivatives (symmetric or unsymmetric) for the quantitative and qualitative detection of $Zn^{2+}$ (FIG. 16). Compound (1) represents the preferred embodiment of the invention which works through an internal charge transfer mechanism. In that case, it is desirable to have a more conjugated system which will lead to a longer wavelength. To achieve ICT the domain responsible for $Zn^{2+}$ should be electron rich and the domain remote from the $Zn^{2+}$ should be electron deficient. The wavy line in FIG. 15 may be branched leading to more than one electron deficient domain. Many derivatives of compounds (3), (4), (5), (6), (12), (13), (14), (17) and (18), as illustrated in the drawings have been prepared and/or are under study. Examples of those structures are Compounds (13) and (14) and their asymmetric counterparts, where independently from each other, the fused functional groups, independent from each other, are selected from the group consisting of phenyl, nitrophenyl, dinitrophenyl, trinitrophenyl phenol, dihydroxy, trihydroxyphenyl, napthyl, nitronapthylene, anthraceneyl, pyreneyl, amino acid, peptide, pyranosyl, cyclopropyl, cyclobutyl, cyclopentyl, cyclohexyl, cycloheptyl, cyclooctyl, cyclononyl, cyclodecyl, [4.4.0]cyclodecane, [2.2.1]cycloheptane, pyridinyl, quinolinyl, acridinylthe; and the non-fused functional groups are selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl).

The equivalent derivatives of the linked compounds (17) and (18) with the same functional groups in the non-fused positions are of interest and are also being disclosed and claimed herein. The linkers between the two, three, four, or five dipyrryn molecules, for compounds (17) and (18), independently from each other, are selected from the group consisting of $C_1$-$C_{15}$ alkyl, amino acid, peptide, pyranosyl, cyclopropyl, cyclobutyl, cyclopentyl, cyclohexyl, cycloheptyl, cyclooctyl, cyclononyl, cyclodecyl, [4.4.0]cyclodecane, 1,3-dibutenyl, 1,3,5-trihexenyl, 1,3,5,7-tetraoctenyl, 1,3,5,7,9-pentadecenyl, phenyl, nitrophenyl, dinitrophenyl, trinitrophenyl phenol, dihydroxy, trihydroxyphenyl, napthyl, nitronapthylene, anthraceneyl, pyreneyl, pyridinyl, quinolinyl, acridinyl, n-alkyl n-alkenyl and cycloalkane.

The invention claimed is:

1. A composition suitable for quantitative and qualitative sensing of +2 transition metals using ratiometric fluorescence capable of forming a stable transition metal complex through internal charge transfer with a target transition metal, and fluorescing in a measurable manner in the presence of the target transition metal, comprising:
   a. a metal binding, electron donating dipyrrin functionality;
   b. an electron withdrawing functionality, wherein the electron donating functionality is linked to the electron withdrawing functionality; and
   c. an attachment base to which the chemosensor can be fixedly attached, the composition comprising the formula:

wherein $R^3$ and $R^5$ comprise phenyl groups, $R^4$ comprises a 2-(8-hydroxyquinoline)group, and $R^1$ and $R^2$, and $R^6$ and $R^7$ comprise fused 1,2(7-methoxytetrahydronaphthalene).

2. The composition according to claim 1 wherein $R^2$ and $R^3$, and $R^5$ and $R^6$, independently from each other, are selected from the group of fused structures consisting of phenyl, 1,2-(4-nitrophenyl), 1,2-(di-4,6-nitrophenyl), 1,2-(tri-4,5,6-nitrophenyl) 1,2-(phen-4-ol), 1,2-(di-4,6-hydroxyphenyl), 1,2-(tri-4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl; and
   $R^1$, $R^4$ and $R^7$, independently from each other, are selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

3. The composition according to claim 1 wherein $R^1$ and $R^2$, and $R^6$ and $R^7$, independently from each other, are selected from the group of fused structures consisting of phenyl, 1,2-(4-nitrophenyl), 1,2-(di-4,6-nitrophenyl), 1,2-(tri-4,5,6-nitrophenyl) 1,2-(phen-4-ol), 1,2-(di-4,6-hydroxyphenyl), 1,2-(tri-4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl 1-pyreneyl, 2-pyreneyl, Leucine connected through N and C termini, 1,4-pyranosyl, 1,2-cyclopropyl, 1,2-cyclobutyl, 1,2-cyclopentyl, 1,2-cyclohexyl, 1,2-cycloheptyl, 1,2-cyclooctyl, 1,2-cyclononyl, 1,2-cyclodecyl, 1,2-[4.4.0]cyclodecane, 1,2-[2.2.1]cycloheptane, 1,2(4-pyridinyl), 1,2-(4-quinolinyl), 1,2-(9-acridinyl) and $R^3$, $R^4$ and $R^5$, independently from each other, are selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1[-4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

4. The composition according to claim 1 wherein $R^2$ and $R^3$, and $R^6$ and $R^7$, independently from each other, are selected from the group of fused structures consisting of phenyl, 1,2-(4-nitrophenyl), 1,2-(di-4,6-nitrophenyl), 1,2-(tri-4,5,6-nitrophenyl) 1,2-(phen-4-ol), 1,2-(di-4,6-hydroxyphenyl), 1,2-(tri-4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl, cyclohexyl and $R^1$, $R^4$ and $R^5$, independently from each other, are selected from the group consisting of hydrogen, alcohol, methoxy, $C_1$-C, alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

5. The composition according to claim 1 wherein $R^1$ and $R^2$, and $R^5$ and $R^6$, independently from each other, are selected from the group of fused structures consisting of phenyl, 1,2-(4-nitrophenyl), 1,2-(di-4,6-nitrophenyl), 1,2-(tri-4,5,6-nitrophenyl) 1,2-(phen-4-ol), 1,2-(di-4,6-hydroxyphenyl), 1,2-(tri-4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl; and $R^3$, $R^4$ and $R^7$, independently from each other, are selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4, 6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

6. The composition according to claim 1 wherein $R^1$, $R^2$, $R^3$, $R^5$, $R^6$ and $R^7$, are hydrogen, and $R^4$ is selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

7. The composition according to claim 1 wherein $R^2$ and $R^3$, and $R^5$ and $R^6$, independently from each other, are selected from the group of fused structures consisting of phenyl, 1,2-(4-nitrophenyl), 1,2-(di4,6-nitrophenyl), 1,2-(tri4,5,6-nitrophenyl) 1,2-(phen-4-ol), 1,2-(di4,6-hydroxyphenyl), 1,2-(tri4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl; $R^1$ and $R^2$ are hydrogen and $R^4$ is selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

8. The composition according to claim 1 wherein $R^1$ and $R^2$, and $R^6$ and $R^7$, independently from each other, are selected from the group of fused structures consisting of phenyl, 1,2-(4-nitrophenyl), 1,2-(di4,6-nitrophenyl), 1,2-(tri4,5,6-nitrophenyl) 1,2-(phen-4-ol), 1,2-(di4,6-hydroxyphenyl), 1,2-(tri4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl; $R^3$ and $R^6$ are hydrogen and $R^4$ is selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

9. The composition according to claim 1 wherein $R^2$ and $R^3$, and $R^6$ and $R^7$, independently from each other, are selected from the group of fused structures consisting of phenyl, 1,2-(4-nitrophenyl), 1,2-(di4,6-nitrophenyl), 1,2-(tri4,5,6-nitrophenyl) 1,2-(phen-4-ol), 1,2-(di4,6-hydroxyphenyl), 1,2-(tri4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl; $R^1$ and $R^5$ are hydrogen and $R^4$ is selected from the group consisting of hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

10. The composition according to claim 1 wherein $R^1$ and $R^2$, and $R^5$ and $R^6$, independently from each other, are selected from the group of fused structures consisting of phenyl, 1,2-(4-nitrophenyl), 1,2-(di4,6-nitrophenyl), 1,2-(tri4,5,6-nitrophenyl) 1,2-(phen-4-ol), 1,2-(di4,6-hydroxyphenyl), 1,2-(tri4,5,6-hydroxyphenyl), 1,2-napthyl, 1,2-(nitro-3-napthylene), 1,2-anthraceneyl, 1,2-pyreneyl, 1,2-cyclohexyl, 1,2-pyridinyl, 1,2-quinolinyl, 1,2-acridinyl; $R^3$ and $R^7$ are hydrogen and $R^4$ is selected from the group consisting of hydrogen, alcohol, methoxy, $C_1$-C, alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, Leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclononyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

11. The composition according to claim 1 wherein $R^2$, $R^3$, $R^5$ and $R^6$ are hydrogen; and $R^1$, $R^4$ and $R^7$, independently from each other, are selected from the group consisting of hydroxyl, methoxy, tert-butyl, isobutyl and isopropyl, hydrogen, alcohol, methoxy, $C_1$-$C_7$ alkyl, nitro, phenyl, nitro-4-phenyl, di-2,4-nitrophenyl, tri-2,4,6-nitrophenyl phen-4-ol, di-2,4-hydroxy, tri-2,4,6-hydroxyphenyl, 1-napthyl, 2-napthyl, nitronapthylene, 1-anthraceneyl, 2-anthraceneyl, 3-anthraceneyl, 1-pyreneyl, 2-pyreneyl, leucine attached at the nitrogen, peptide, 1-pyranosyl, 1-cyclopropyl, 1-cyclobutyl, 1-cyclopentyl, 1-cyclohexyl, 1-cycloheptyl, 1-cyclooctyl, 1-cyclonoriyl, 1-cyclodecyl, 1-[4.4.0]cyclodecane, 1-[2.2.1]cycloheptane, 4-pyridinyl, 4-quinolinyl, 9-acridinyl, 1-(4-phenyl(1,3-dibutenyl)), 1-(6-phenyl (1,3,5-trihexenyl), 1-(8-phenyl (1,3,5,7-tetraoctenyl) and 1-(10-phenyl 1,3,5,7,9-pentadecenyl), 1-glucosyl.

12. The composition according to claim 1 wherein the attachment base comprises materials selected from a group consisting of glass, plastic, quantum dots and polymer.

13. The composition according to claim 5 wherein the attachment base comprises materials selected from a group consisting of glass, plastic, quantum dots and polymer.

* * * * *